(12) United States Patent
Berg

(10) Patent No.: US 11,406,529 B2
(45) Date of Patent: Aug. 9, 2022

(54) COOLING SYSTEM FOR CIRCULATING COOLING FLUID IHROUGH A COOLING PAD

(71) Applicant: BrainCool AB, Lund (SE)

(72) Inventor: Jon Berg, Dalby (SE)

(73) Assignee: BrainCool AB, Lund (SE)

( * ) Notice: Subject to any disclaimer, the term of this patent is extended or adjusted under 35 U.S.C. 154(b) by 875 days.

(21) Appl. No.: 16/305,663

(22) PCT Filed: May 31, 2017

(86) PCT No.: PCT/EP2017/063169
§ 371 (c)(1),
(2) Date: Nov. 29, 2018

(87) PCT Pub. No.: WO2017/207636
PCT Pub. Date: Dec. 7, 2017

(65) Prior Publication Data
US 2020/0323681 A1    Oct. 15, 2020

(30) Foreign Application Priority Data

Jun. 2, 2016 (SE) .................................... 1650772-5

(51) Int. Cl.
*A61F 7/00* (2006.01)
(52) U.S. Cl.
CPC .... *A61F 7/0085* (2013.01); *A61F 2007/0002* (2013.01); *A61F 2007/0018* (2013.01); *A61F 2007/0039* (2013.01); *A61F 2007/0056* (2013.01); *A61F 2007/0093* (2013.01)

(58) Field of Classification Search
CPC .............................................. A61F 2007/0056
See application file for complete search history.

(56) References Cited

U.S. PATENT DOCUMENTS

| 3,007,473 A | 11/1961 | Jackson et al. |
| 3,683,902 A | 8/1972 | Artemenko et al. |
| 2004/0068310 A1* | 4/2004 | Edelman .................. A61F 7/02 607/104 |
| 2014/0222121 A1 | 8/2014 | Spence et al. |
| 2014/0277302 A1 | 9/2014 | Weber et al. |

FOREIGN PATENT DOCUMENTS

| EP | 0144877 A2 | 6/1985 |
| JP | 2013138764 A | 7/2013 |
| KR | 1020140053680 A | 5/2014 |
| WO | 2013/190337 A1 | 12/2013 |
| WO | 2016/016610 A1 | 2/2016 |
| WO | 2017/085272 A1 | 5/2017 |

\* cited by examiner

*Primary Examiner* — Kaitlyn E Smith
(74) *Attorney, Agent, or Firm* — Capitol City TechLaw

(57) ABSTRACT

A cooling system (1) for use in a non-invasive medical cooling process to cool at least one portion of the body of a person (2) by means of a cooling fluid flowing through a cooling pad (3), comprising a first pump 70, a fluid outlet conduit (20), a fluid inlet conduit (40 and; —a second pump (80) arranged to pump cooling fluid through a fluid bypass conduit (60) from the fluid inlet conduit (40) to the fluid outlet conduit (20), wherein—the cooling system (1) is arranged such that cooling fluid is transported from the tank (10) to the fluid outlet conduit (20) when the first pump (70) is operated and such that cooling fluid is transported from the fluid inlet conduit (40) to the fluid outlet conduit when the second pump (80) is operated.

4 Claims, 1 Drawing Sheet

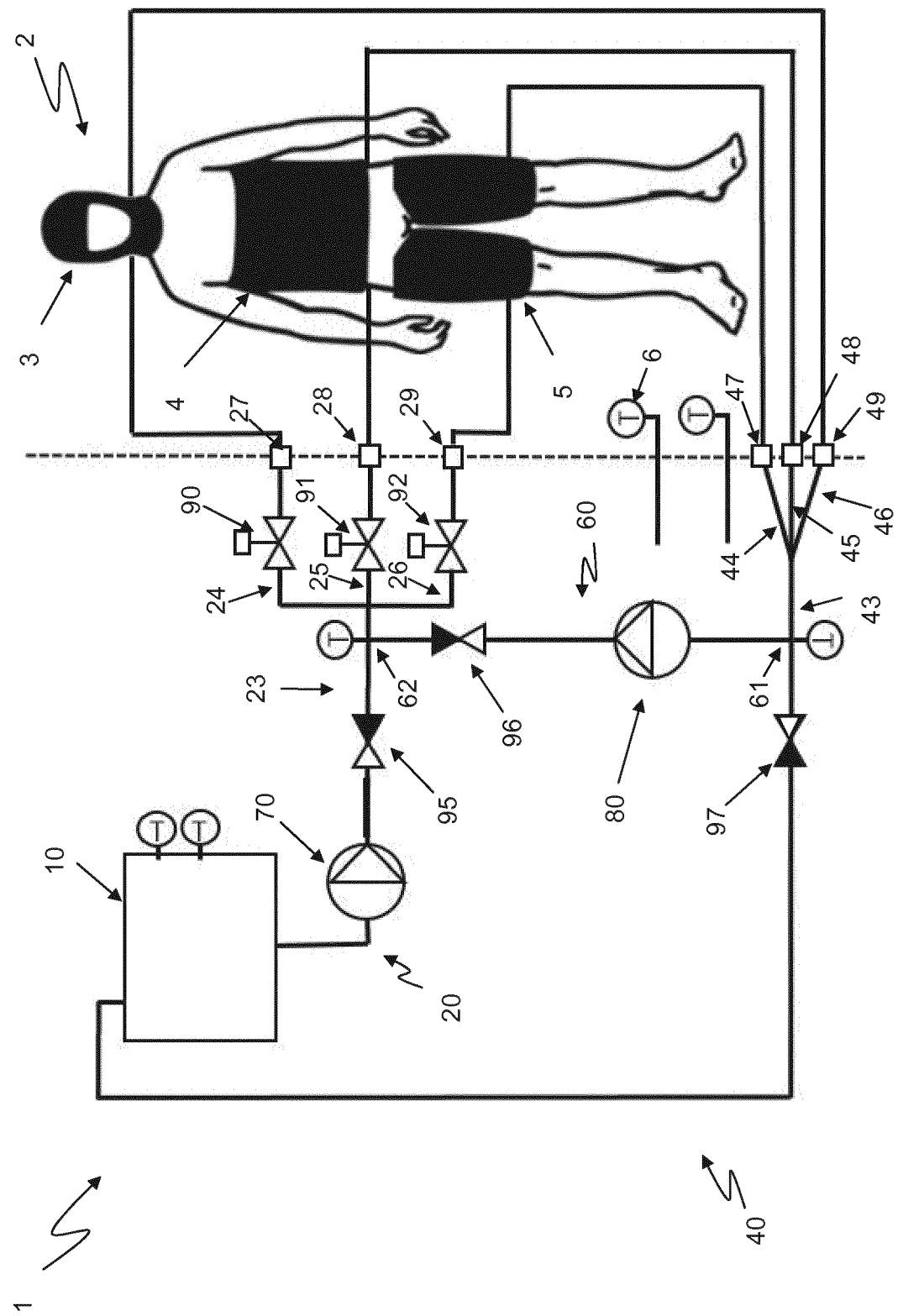

COOLING SYSTEM FOR CIRCULATING COOLING FLUID IHROUGH A COOLING PAD

This application claims priority under 35 USC 119(a)-(d) to SE patent application No. 1650772-5, which was filed on Jun. 2, 2016, the entire contents of which are incorporated herein by reference.

TECHNICAL FIELD

The present disclosure relates to a cooling system for use in a non-invasive medical cooling process to cool at least one portion of the body of a person by means of a cooling fluid flowing through a cooling pad.

BACKGROUND ART

Cooling pads may be used in medical cooling processes for medically cooling various regions of the body of a person or patient in a non-invasive manner by placing the cooling pad onto or around the body part to be cooled. The largest available cooling areas for a non-invasive cooling system are located on the back or chest of the patient The cooling pads are typically connected to a cooling system which circulates cooling fluid through the cooling pads. The known cooling systems comprise a reservoir which maintains the cooling fluid at a constant temperature and a pump for circulating the cooling fluid through the cooling pads. One example of a known cooling system is US2002/020317. Another cooling system is shown in WO2016/016610.

A person suffering from e.g. cardiac arrest may be subject to non-invasive medical cooling. A general effect of such treatment is that the body of the patient will start to shiver as a result of the cooling. Under normal conditions when the body temperature decreases beyond a certain point, e.g. around 35° C., the body starts to shiver in an attempt of regaining the heat loss. Depending on the person involuntary shivering may be initiated at different temperatures. Shivering is undesirable since it consumes the patient's forces. Moreover, under prolonged cooling treatment the patient may also have a fever and in that case the cooling treatment may result in even higher body temperatures.

To avoid shivering of a patient, cooling systems may be provided with heating circuits to control the temperature of the cooling fluid. Such heating systems includes heaters, mixing tanks and heat exchanger which makes the known cooling systems complicated and bulky and also increases the cost for manufacturing and maintenance of the cooling system.

Thus, it is an object of the present disclosure to provide an improved cooling system for use in a non-invasive medical cooling process which solves at least one of the problems in the prior-art. In particular, it is an object of the present disclosure to provide a cooling system which is compact and reliable and that allows for accurate control of the temperature of the cooling fluid. Moreover it is an object of the present disclosure to provide a cooling system which is of simple design and may be produced at relatively low cost.

SUMMARY OF THE DISCLOSURE

According to the disclosure, at least one of these objects are met by a cooling system for use in a non-invasive medical cooling process to cool at least one portion of the body of a person by means of a cooling fluid flowing through a cooling pad, comprising:
  a tank for holding cooling fluid;
  a fluid outlet conduit, connected to the tank and having an outlet portion configured to be connected to an inlet for cooling fluid of at least a first cooling pad;
  a fluid inlet conduit, connected to the tank and having an inlet portion configured to be connected to an outlet for cooling fluid of at least a first cooling pad;
  a first pump arranged to pump cooling fluid through the fluid outlet conduit from the tank to the outlet portion,
  a fluid bypass conduit connected to the inlet portion of the fluid inlet conduit and to the outlet portion of the fluid outlet conduit, thereby bypassing the tank, wherein the fluid bypass conduit, has a first end connected to the inlet portion of fluid inlet conduit and a second end connected to the outlet portion of the fluid outlet conduit and;
  a second pump arranged between the first and the second ends of the fluid bypass conduit to pump cooling fluid through the fluid bypass conduit from the fluid inlet conduit to the fluid outlet conduit, characterized in,
  a first non-return valve is arranged between the second end of the fluid bypass conduit and the first pump to prevent cooling fluid from flowing in direction towards the first pump and;
  a second non-return valve arranged between the second end of the fluid bypass conduit and the second pump to prevent cooling fluid from flowing in direction towards the second pump wherein,
  the cooling system is arranged such that cooling fluid is transported from the tank to the outlet portion of the fluid outlet conduit when the first pump is operated and such that cooling fluid is transported from the inlet portion of the fluid inlet conduit to the fluid outlet portion of the fluid outlet conduit when the second pump is operated.

In the cooling system of the present disclosure the fluid bypass conduit allows all cooling fluid to be circulated directly from the inlet opening of the fluid inlet conduit to the outlet opening of the fluid outlet openings without passing through the coolant tank. When the cooling fluid is circulated in this manner it has been surprisingly found that sufficient mixing of the cooling fluid is achieved in the cooling pads. That is, at the same time the cooling fluid in the cooling pads removes heat from the skin of the patient it is mixed and rapidly assumes a temperature close to the temperature of the skin temperature of the patient.

Since the temperature of the cooling pads is held close to the skin temperature of the patient, the patient may be sufficiently cooled without any adverse effects in terms of shivering or fevers. In particular, it is avoided that excessive cooling of a feverish patient will result in a rise of the fever. Moreover, in feverish persons the body temperature, or the so called fever curve, may vary over time. However, the temperature of the cooling pads will rapidly adjust to any temperature changes of the patient's skin and remain close to the fever curve of the person.

An additional advantage of the cooling system according to present disclosure is that cooling fluid may be selectively supplied to the three cooling pads. Either from the tank or from the fluid bypass conduit. This provides the possibility to selectively direct cooling fluid to areas of the body with more or less cold receptors and thereby a high degree of flexibility in the cooling of the patient.

Thus, the cooling system according to the present disclosure facilitates, with a simple and compact design, to maintain an effective control of the temperature of the cooling fluid of the cooling pads.

further, features and alternatives of the cooling system are disclosed in the following detailed description and the appended claims.

BRIEF DESCRIPTION OF THE DRAWINGS

FIG. 1: A schematic drawing of a cooling system according to a preferred embodiment of the present disclosure.

DETAILED DESCRIPTION OF EMBODIMENTS

The cooling system according to the present disclosure will now be described more fully hereinafter. The cooling system according to the present disclosure may however be embodied in many different forms and should not be construed as limited to the embodiments set forth herein. Rather, these embodiments are provided by way of example so that this disclosure will be thorough and complete, and will fully convey the scope of the present disclosure to those persons skilled in the art. Same reference numbers refer to same elements throughout the description.

FIG. 1 shows a schematic drawing of the cooling system 1 according to the present disclosure. The cooling system 1 is intended for use in a non-invasive medical cooling process to cool at least one portion of the body of a person 2 by means of a cooling fluid flowing through a cooling pad 3, 4, 5. Each cooling pad has an inlet opening (not shown) for introducing the flow of cooling liquid into the cooling pad and an outlet opening (not shown) for letting the flow of cooling liquid out of the cooling pad. The cooling pads may be manufactured of opposing sheets of silicon and designed to contain a suitable volume of cooling liquid, for example 2-5 $cm^3$. The cooling pads may further be configured to a cause a turbulent flow of the cooling liquid trough the cooling pad, thus ensuring good mixing and effective heat transfer between the cooling liquid and the skin of the patient. A cooling pad suitable for the cooling system of the present disclosure is described in applicant's non-published Swedish patent application 1551499-5.

The cooling system comprises a tank 10 for holding cooling fluid, which may be water or a mixture of water and MPG glycol. The tank may also comprise a heat exchanger unit (not shown) for maintaining the temperature of the cooling fluid at predetermined level, for example 4° C.

The cooling system 1 comprises a fluid outlet conduit 20 for transporting cooling fluid from the tank 10 to the cooling pads 3, 4, 5. The fluid outlet conduit 20 is connected to the tank 10 and comprises a first pump 70 for pumping cooling fluid through the fluid outlet conduit 20. The pump may be a centrifugal pump. The fluid outlet conduit 20 further comprises an outlet portion 23 which extends from the first pump 70 and terminates in at least one outlet opening 27 which is configured to be liquid tight connected to an inlet opening of at least one cooling pad. In the disclosed embodiment, the outlet portion 23 comprise three outlet branches 24, 25, 26 which each terminates in an outlet opening 27, 28, 29.

At least one valve means 90, 91, 92, for example an on/off valve, may be provided in the outlet portion 23 in order to close at least one outlet opening 27, 28, 29. In FIG. 1 each of the branches 24-26 has a valve means 90, 91, 92 in the form of an on/off valve for closing the fluid outlet 27, 28, 29 of each branch. The valve means 90, 91, 92 may be operated independent from each other and thus allowing for selective closing of the outlet openings 27, 28, 29.

The cooling system 1 further comprises a fluid inlet conduit 40 which extends from the tank 10 to an inlet portion 43 which terminates in at least one inlet opening 47 which is configured to be liquid tight connected to an outlet opening of at least one cooling pad. In the described embodiment the inlet portion 43 comprise three inlet branches 44, 45, 46 which each terminates in an inlet opening 47, 48, 49.

Thus, cooling liquid is supplied from the tank 10 and may be pumped by the first pump 70 through the fluid outlet conduit 20 to the cooling pads 110, 120, 130 and returned from the cooling pads 110, 120, 130 to the tank 10 through the fluid inlet conduit 40.

According to the present disclosure, the cooling system 1 comprises a fluid bypass conduit 60 which is connected to the fluid inlet portion 43 of the fluid inlet conduit 40 and to the fluid outlet portion 23 of the fluid outlet conduit 20. The cooling system 1 further comprises a second fluid pump 80, which is arranged to pump cooling fluid from the inlet portion 43 of the fluid inlet conduit 40 to the outlet portion 23 of the fluid outlet conduit 20. The cooling system 1 is arranged such that all cooling fluid is transported from the tank 10 to the outlet portion 23 of the fluid outlet conduit 20 when the first pump 70 is operated. The cooling system 1 is further arranged such that all cooling fluid is transported from the inlet portion 43 of the fluid inlet conduit 40 to the fluid outlet portion 23 of the fluid outlet conduit 20 when the second pump 80 is operated.

The fluid bypass conduit 60 thereby comprises a first end 61 and a second end 62. The first end 61 is connected to the inlet portion 43 of the fluid inlet conduit 40 and the second end 62 is connected to the outlet portion 23 of the fluid outlet conduit 20.

The second pump 80 is arranged in the fluid bypass conduit 60, between the first and the second ends 61, 62 thereof. The second pump 80 is arranged such that it pumps fluid in direction from the first end 61 of the fluid bypass channel 60 to second end 62 of the fluid bypass channel 60. The cooling system 1 further comprises three non-return valves 95, 96, 97 for controlling the flow of cooling fluid when the first and the second pumps 70, 80 are operated. A non-return valve allows flow of fluid in one direction through the valve but prevents flow of fluid through the valve in the opposite direction.

A first non-return valve 95 is arranged in the outlet portion 23 of the fluid outlet conduit 20. The first non-return valve 95 is thereby arranged between the first fluid pump 70 and the second end 62 of the fluid bypass conduit 60. The first non-return valve 95 is arranged to prevent cooling fluid from flowing in direction from the second end 62 of the fluid bypass conduit towards the first fluid pump 70.

Thus, the second end 62 of the fluid bypass conduit 60 is arranged between the first non-return valve 95 and the outlet openings 27, 28, 29 of the outlet portion 23. In particular, the second end 62 of the fluid bypass conduit 60 is arranged between the valve means 90, 91, 92 of the outlet portion 23 and the first non-return valve 95.

A second non-return valve 96 is arranged in the fluid bypass conduit 60 in a position between the second end 62 of the fluid bypass conduit 60 and the second pump 80. The second non-return valve 96 is arranged to prevent cooling fluid from flowing in direction from the second end 62 of the fluid bypass conduit 60 towards the second fluid pump 80.

A third non-return valve 97 is arranged in the fluid inlet channel 40 in a position between the tank 10 and the first end 61 of the fluid bypass conduit 60. The second non-return valve 96 is arranged to prevent cooling fluid from flowing in direction from the tank 10 towards the fluid bypass conduit 60.

Thus the first end 61 of the fluid bypass conduit 60 is arranged between the inlet openings 47, 48, 40 of the fluid inlet portion 40 and the third non-return valve 97.

In the following the operation of the cooling system 1 according to the present disclosure will be described.

The cooling system 1 may be operated in a first cooling mode in which strong cooling is provided to patient 2. In the first cooling mode, the second pump 80 is off, i.e. inactive and does thus not pump cooling liquid. The three valve means 90, 91, 92 may be in open position and thus allowing flow of cooling fluid into the three cooling pads 3, 4, 5. The first pump 70 is operated, i.e on and pumps cooling liquid from the tank 10 through the fluid outlet conduit 20, to the fluid outlets 27, 28, 29 and into the cooling pads 3, 4, 5. During operation of the first pump 70, the second non-return valve 96 prevents cooling fluid from flowing through the fluid bypass conduit 60. The cooling liquid returns from the cooling pads 3, 4, 5 via the fluid inlet openings 47, 48, 49 and is returned to the tank 10 through fluid inlet conduit 40. In the first cooling mode the cooling liquid is continuously re-circulated in the tank 10 and is therefore be held at a constant low temperature, e.g. 4° C. The body core temperature of the patient 2 may be monitored during cooling, by a temperature sensor 6. When a set target core temperature value is reached the cooling of the patient 2 may be reduced to avoid shivering by closing one or more of the valve means 90, 91, 92. For example valve 91 may be closed with the result that cooling is decreased on the patient's chest and around the armpits. It is also possible to repeatedly open and close one or more of the valve means 90, 91, 92 to reduce cooling of the patient.

In the second cooling mode, the object is to hold the cooling pads 3, 4, 5 at a temperature close to the skin temperature of the patient in order to avoid cooling effects that will cause fever. Thus, in the second cooling mode, the first fluid pump 70 is off, i.e. inactive and the second fluid pump 80 is operated, i.e. on. The second fluid pump 80 thereby pumps all the cooling fluid that flows into the fluid inlet conduit 40 from the cooling pads 3, 4, 5 directly through the fluid bypass conduit 60 and into the fluid outlet portion 23 the fluid outlet line 20 and into the cooling pads 3, 4, 5. The cooling fluid will therefore circulate through the cooling pads and is not mixed with cooling liquid in the tank 10. The cooling temperature will therefore rapidly assume the skin temperature of the patient 2.

The cooling system 1 may also be operated in a third cooling mode, which provides mild cooling to a patient having a fever. In this case the cooling system is operated as in the second mode but only valve means 92 is open. This will result in that cooling fluid is only circulated though cooling pad 5 which cools the thighs of the patient. The thighs have few cold receptors and selective circulation of cooling fluid in this region will result in that the temperature of the cooling pad 5 is held close to the fever curve of the patient.

Although a particular embodiment has been disclosed in detail this has been done for purpose of illustration only, and is not intended to be limiting. In particular it is contemplated that various substitutions, alterations and modifications may be made within the scope of the appended claims.

In particular it is appreciated that by "fluid outlet conduit" and "fluid inlet conduit" is meant a continuous channel for transporting cooling fluid.

In particular it is appreciated that the fluid outlet conduit may comprise a first conduit section extending from the tank 10 to the first pump 70 and a second conduit section that extends from the pump 70 to the first non-return valve 95; a third conduit section may extend from the first non-return valve 95 to an outlet opening 27, 28, 29; the third conduit may also extend from the first non-return valve 95 to two or three or more conduit branches 24, 25, 26 which terminates in an outlet opening 27, 28, 29.

The fluid inlet conduit 40, may comprise a first conduit section that extends from the tank 10 to the third non-return valve 97; a second conduit section may extend from the third non-return valve 97 to an inlet opening 47, 48, 49; the second conduit section may also extend from the third non-return valve 97 to two or three or more conduit branches 44, 45, 46 which each terminates in an inlet opening 47, 48, 49.

The fluid bypass conduit 60 may comprise a first conduit section which extends from the second conduit of the fluid inlet conduit 40 to the second pump 80; a second conduit section that extends from the second pump 80 to a second non-return valve 96 and a third conduit section that extends from the second non-return valve 96 to the second conduit section of the fluid outlet conduit 40.

The conduit sections disclosed above may be in the form of pipe or tube or tubing.

Moreover, although specific terms may be employed herein, they are used in a generic and descriptive sense only and not for purposes of limitation. Furthermore, as used herein, the terms "comprise/comprises" or "include/includes" do not exclude the presence of other elements. Finally, reference signs in the claims are provided merely as a clarifying example and should not be construed as limiting the scope of the claims in any way.

The invention claimed is:

1. A cooling system for use in a non-invasive medical cooling process to cool at least one portion of the body of a person by means of a cooling fluid flowing through a cooling pad, the cooling system comprising:
   a tank for holding cooling fluid;
   a fluid outlet conduit connected to the tank and having an outlet portion configured to be connected to an inlet for cooling fluid of at least a first cooling pad;
   a fluid inlet conduit connected to the tank and having an inlet portion configured to be connected to an outlet for cooling fluid of at least the first cooling pad;
   a first pump arranged to pump cooling fluid through the fluid outlet conduit from the tank to the outlet portion;
   a fluid bypass conduit connected to the inlet portion of the fluid inlet conduit and to the outlet portion of the fluid outlet conduit, thereby bypassing the tank, wherein the fluid bypass conduit has a first end connected to the inlet portion of fluid inlet conduit, and a second end connected to the outlet portion of the fluid outlet conduit;
   a second pump arranged between the first and the second ends of the fluid bypass conduit to pump cooling fluid through the fluid bypass conduit from the fluid inlet conduit to the fluid outlet conduit;
   a first non-return valve arranged between the second end of the fluid bypass conduit and the first pump to prevent cooling fluid from flowing in a direction from the second end towards the first pump; and
   a second non-return valve arranged between the second end of the fluid bypass conduit and the second pump to prevent cooling fluid from flowing in a direction from the second end towards the second pump;

wherein cooling fluid is transported from the tank to the outlet portion of the fluid outlet conduit when the first pump is operated; and wherein cooling fluid is transported from the inlet portion of the fluid inlet conduit to the outlet portion of the fluid outlet conduit when the second pump is operated.

2. The cooling system according to claim 1, wherein the outlet portion of the fluid outlet conduit comprises at least a first valve means for closing and opening at least a first fluid outlet of the outlet portion.

3. The cooling system according to claim 1, wherein a third non-return valve is arranged between the first end of the fluid bypass conduit and the tank to prevent cooling fluid from flowing in a direction from the tank towards the fluid bypass conduit.

4. The cooling system according to anyone of claim 1, wherein the first and the second pumps are controlled individually, such that the first pump is operated when the second pump is inactive, and such that the second pump is operated when the first pump is inactive.

\* \* \* \* \*